United States Patent
Joy

(10) Patent No.: US 11,461,596 B2
(45) Date of Patent: *Oct. 4, 2022

(54) METHODS AND APPARATUS TO ADAPT MEDICAL IMAGING INTERFACES BASED ON LEARNING

(71) Applicant: General Electric Company, Schenectady, NY (US)

(72) Inventor: Manuel Joy, Chicago, IL (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/070,468

(22) Filed: Oct. 14, 2020

(65) Prior Publication Data

US 2021/0056359 A1 Feb. 25, 2021

Related U.S. Application Data

(63) Continuation of application No. 16/021,939, filed on Jun. 28, 2018, now Pat. No. 10,824,912.

(51) Int. Cl.
*G06K 9/62* (2022.01)
*G16H 30/20* (2018.01)
*A61B 5/00* (2006.01)
*G06N 3/04* (2006.01)
(Continued)

(52) U.S. Cl.
CPC .......... *G06K 9/6262* (2013.01); *A61B 5/7267* (2013.01); *G06K 9/6256* (2013.01); *G06K 9/6267* (2013.01); *G06N 3/04* (2013.01); *G06N 3/08* (2013.01); *G06T 7/0016* (2013.01); *G16H 30/20* (2018.01); *G06T 2207/20081* (2013.01)

(58) Field of Classification Search
CPC .. G06K 9/6262; G06K 9/6256; G06K 9/6267; A61B 5/7267; G06N 3/04; G06N 3/08; G06T 7/0016; G16H 30/20
USPC .......................................................... 382/128
See application file for complete search history.

(56) References Cited

U.S. PATENT DOCUMENTS 10,824,912 B2 * 11/2020 Joy ........................ G16H 40/67
2010/0131874 A1 5/2010 Linthicum et al.
(Continued)

OTHER PUBLICATIONS

Patent Cooperation Treaty, "International Search Report and Written Opinion," issued in connection with PCT Application No. PCT/US2019/038874, dated Sep. 26, 2019, 15 pages.
(Continued)

*Primary Examiner* — Ayodeji O Ayotunde
(74) *Attorney, Agent, or Firm* — Hanley, Flight & Zimmerman

(57) ABSTRACT

Methods and apparatus to adapt medical imaging interfaces based on learning are disclosed. An example apparatus includes a use monitor to monitor, in a first session, user actions and medical content data pertaining to operation of a clinical image display, a learning device including a processor to implement a learning network to develop a model for a subsequent session based on the user actions in relationship to a context of the medical content data. The model developed by defining contextual patterns of the user actions based on the context and the medical content data. The learning device is to update, prior to or during a second session subsequent the first session, a user interface based on the model.

20 Claims, 14 Drawing Sheets

(51) Int. Cl.
    *G06N 3/08*    (2006.01)
    *G06T 7/00*    (2017.01)

(56) References Cited

U.S. PATENT DOCUMENTS

2016/0259501 A1    9/2016    Nagarajan et al.
2020/0005088 A1    1/2020    Joy

OTHER PUBLICATIONS

Jorritsma et al., "Adaptive Support for User Interface Customization: A Study in Radiology," May 2015, International Journal of Human-Computer Studies, vol. 77, 9 pages.

Patel et al., "Interface Design for Health Care Environments: The Role of Cognitive Science," 1998, Proceedings, AMIA Symposium, 9 pages.

Vasilyeva et al., "Towards the Framework of Adaptive User Interfaces for eHealth," 2005, Proceedings of the 18th IEEE Symposium on Computer-Based Medical Systems (CBMS'05), 6 pages.

Langley et al., "Machine Learning for Adaptive User Interfaces," 2005, Part of the Lecture Notes in Computer Science book series (LNCS), vol. 1303, 10 pages.

Soh et al., "Deep Sequential Recommendation for Personalized Adaptive User Interfaces," Mar. 13-17, 2017, Proceedings of the 22nd International Conference on Intelligent User Interfaces, 5 pages.

United States Patent and Trademark Office, "Non-Final Office Action," issued in connection with U.S. Appl. No. 16/021,939, dated Feb. 21, 2020, 19 pages.

United States Patent and Trademark Office, "Notice of Allowance and Fee(s) Due," issued in connection with U.S. Appl. No. 16/021,939, dated Aug. 19, 2020, 22 pages.

\* cited by examiner

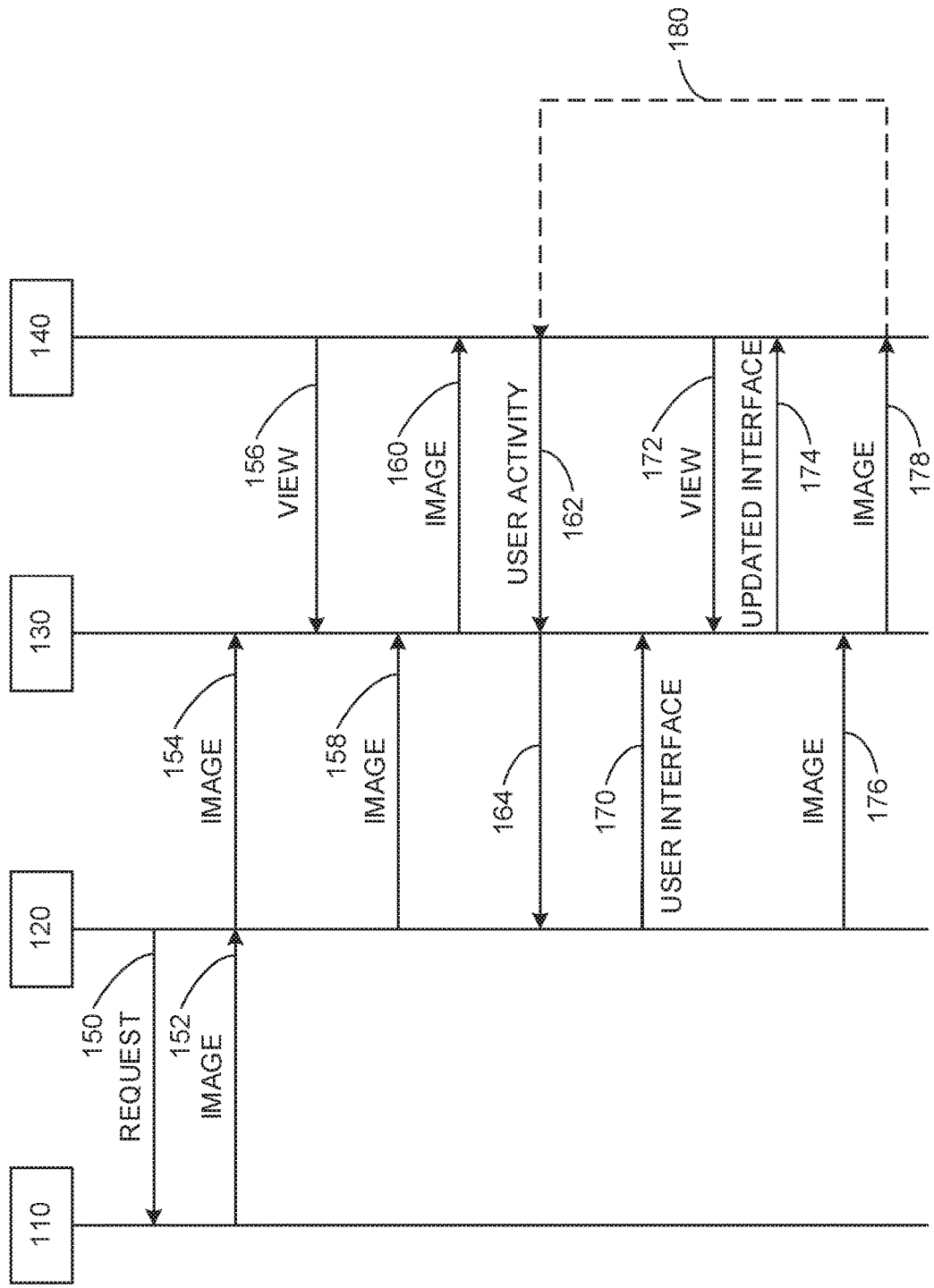

METHODS AND APPARATUS TO ADAPT MEDICAL IMAGING INTERFACES BASED ON LEARNING

RELATED APPLICATION

This patent arises as a continuation of U.S. patent application Ser. No. 16/021,939, which was filed on Jun. 28, 2018. U.S. patent application Ser. No. 16/021,939 is hereby incorporated herein by reference in its entirety. Priority to U.S. patent application Ser. No. 16/021,939 is hereby claimed.

FIELD OF THE DISCLOSURE

This disclosure relates generally to medical imaging systems, and, more particularly, to methods and apparatus to adapt medical imaging interfaces based on learning.

BACKGROUND

Healthcare environments, such as hospitals or clinics, include clinical information systems. Information stored on these systems may include patient medical histories, imaging data, test results, diagnosis information, management information, and/or scheduling information. The information may be centrally stored or divided at a plurality of locations. Healthcare practitioners access patient information or other information at various points in a healthcare workflow.

A reading, such as a radiology or cardiology procedure reading, typically involves a healthcare practitioner, such as a radiologist or a cardiologist, viewing digital images of a patient. In particular, the practitioner performs a diagnosis based on a content of the diagnostic images and reports on the results. Some examples of other tools are prior and related prior exams and their results, laboratory exams, allergies, pathology results, medication, alerts, document images, and other tools.

Typically, a medical imaging system is implemented to provide one or more medical images for examination by a medical professional. For example, the medical imaging system can provide a series of x-ray or MRI images to a display workstation where the images are displayed by a radiologist to perform a diagnostic examination. Based on viewing these images, the radiologist can provide a diagnosis.

SUMMARY

An example apparatus includes a use monitor to monitor, in a first session, user actions and medical content data pertaining to operation of a clinical image display, a learning device including a processor to implement a learning network to develop a model for a subsequent session based on the user actions in relationship to a context of the medical content data. The model developed by defining contextual patterns of the user actions based on the context and the medical content data. The learning device is to update, prior to or during a second session subsequent the first session, a user interface based on the model.

An example method includes to adapt a user interface configuration pertaining to a clinical image display includes monitoring, by executing instructions with a processor, user actions and medical content data during a first session of the clinical image display to define training data. The example method also includes developing, by executing instructions with the processor, a model for a subsequent session based on the user actions in relation to a context of the medical content data with a learning network. The model is developed by defining contextual patterns of the user actions based on the context and the medical content data. The example method also includes adjusting, by executing instructions with the processor, a user interface based on the model prior to or during a second session subsequent the first session.

An example tangible machine readable medium comprising instructions, which when executed, cause a processor to at least define training data based on monitored user actions in relationship to a context of medical content data during operation of a clinical image display in a first session. The example tangible machine readable medium also causes the processor to develop, by a training network, a model for a subsequent session based on the training data. The model is developed by defining contextual patterns of the user actions based on the context and the medical content data. The example tangible machine readable medium also causes the processor to adjust a user interface of the clinical image display based on the model for a second session subsequent the first session.

BRIEF DESCRIPTION OF THE DRAWINGS

FIG. 1B illustrates an example data transfer sequence that can be implemented in the example imaging system of FIG. 1A.

The figures are not to scale. In general, the same reference numbers will be used throughout the drawing(s) and accompanying written description to refer to the same or like parts.

DETAILED DESCRIPTION

Methods and apparatus to adapt medical imaging interfaces based on learning are disclosed. Some known medical imaging interfaces typically require repeated and frequent adjustment of settings and/or image placement by practitioners, such as radiologists or cardiologists. These adjustments can take significant time, thereby increasing costs associated with clinical readings of the images.

Examples disclosed herein utilize machine learning techniques with a learning network to adapt user interfaces to facilitate use of clinical imaging devices. In particular, a learning network is utilized to monitor user actions along with a context of medical content data (e.g., medical case data including image data, patient history data, patient vital signs data, laboratory data, exam data including reason for examination, etc.) to learn a user interface configuration that facilitates use of the clinical imaging device by a clinical practitioner. In other words, the aforementioned learning network is used to analyze the context of the medical content data in view of monitored user actions and the medical content data itself to learn user interface configurations that can be helpful to medical practitioners, thereby saving time for the medical practitioners. Further, examples disclosed herein can streamline imaging viewing by the practitioners (e.g., by caching predicted commands and/or images) to reduce computing resources needed by predicting user commands and/or caching relevant data (e.g., predicted data).

In some examples, image similarity between clinical images of different cases are used to develop a predictive model and/or define a context between user inputs and medical images associated with a medical case history. In some examples, the learned user interface configuration is deployed to a remote viewing display (e.g., the learned user interface is generated at a central server, but deployed to multiple remote viewing workstations). In some examples, a symbol is displayed on a clinical imaging device to represent at least one command (e.g., a batch of commands, viewing setups, etc.) of a learned user interface configuration.

As used herein, the term "context" refers to a contextual relationship (e.g., contextual meaning, contextual commonality, etc.) between medical content data and user inputs or actions (e.g., commands, image arrangements, etc.). As used herein, the term "medical content data" can refer to, but is not limited to, medical files, medical case histories, metadata, diagnoses, patient data, medical image data, medical image types, medical image similarities, key terms, etc. As used herein, the terms "user interface" and "user interface configuration" can refer to icons, a collection of icons, a spatial arrangement of icons, a spatial arrangement of menu items, menu items hierarchies, menu organization, a sequence of commands and/or batched commands, etc.

Figure 1A:
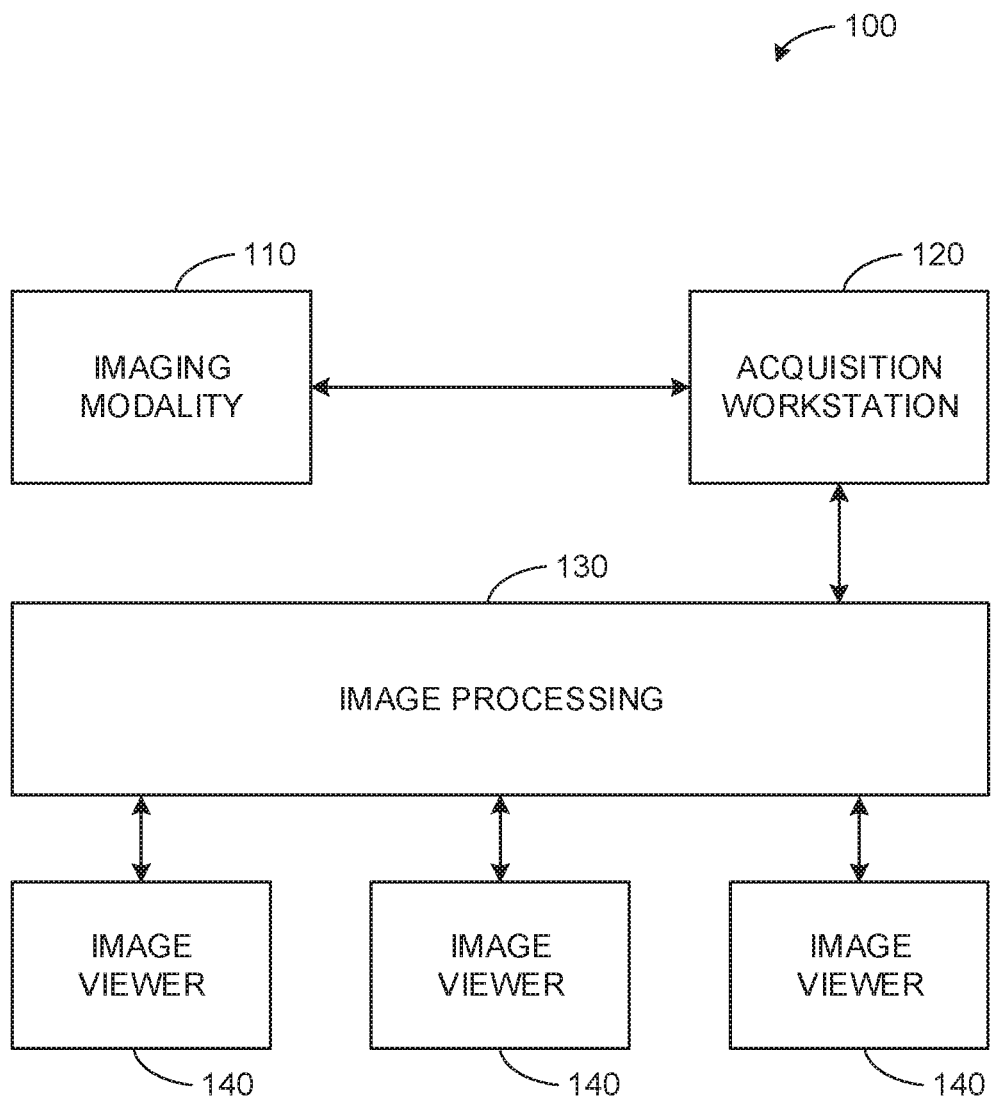
FIG. 1A illustrates an example medical imaging system in which examples disclosed herein can be implemented.

FIG. 1A illustrates an example imaging system 100 that can be implemented with examples disclosed herein. The imaging system 100 includes an imaging modality 110, an acquisition workstation 120, an image processing server 130, and one or more image viewers (e.g., imaging devices including tablets, computers, workstations, mobile phones, remote viewing displays, etc.) 140. The imaging system 100 can include any number of the imaging modalities 110, acquisition workstations 120, the image processing servers 130 and the image viewers 140 and is not in any way limited to the example system 100 illustrated in FIG. 1A. The components of the system 100 can communicate via wired and/or wireless communication, for example, and can be separate systems and/or integrated to varying degrees, for example.

In operation, the example imaging modality 110 obtains one or more images of a patient anatomy. The imaging modality 110 can include any device capable of capturing an image of a patient anatomy, such as a medical diagnostic imaging device, or a server to store images taken by the medical diagnostic imaging device. For example, the imaging modality 110 includes an X-ray imager, ultrasound scanner, magnetic resonance imager, or the like. In this example, image data representative of the image(s) is communicated between the imaging modality 110 and the acquisition workstation 120. The image data is communicated electronically over a wired or wireless connection, for example.

In some examples, the acquisition workstation 120 applies one or more preprocessing functions, for example, to the image data to prepare the image for viewing on an image viewer 140. For example, the acquisition workstation 120 converts raw image data into a Digital Imaging and Communications in Medicine (DICOM) standard format or attach a DICOM header.

The image data is then communicated between the acquisition workstation 120 and the image processing server 130. The image data can be communicated electronically over a wired or wireless connection, for example.

The image viewers 140 can retrieve or receive image data from the image processing server 130 for display to one or more users. For example, one of the image viewers 140 retrieves or receives image data representative of a computed radiography ("CR") image of a patient's chest. A radiologist or user can then examine the image for any objects of interest, such as tumors, lesions, etc., for example.

Healthcare information systems, such as a Hospital Information System (HIS), Radiology Information System (RIS), Cardio-Vascular Information System (CVIS) and/or Picture Archiving and Communication System (PACS), for example, can be implemented in conjunction with examples disclosed herein. The example imaging system 100 and/or PACS stores images from different modalities, such as X-ray, Computed Tomography (CT), Magnetic Resonance (MR), ultrasound, positron emission tomography (PET), etc., while a RIS, CIS or HIS contains non-image information, such as physician reports, disease history, and/or other patient associated data. In order to make a conclusion regarding a reviewed case, a clinician organizes relevant data in a certain order on a set of monitors, for example. In some examples, this order can depend on a plurality of parameters, such as an imaging modality of the exam under review, existence of historical images and number of historical images, previous reports, and/or list of prescribed medications, etc. In some examples, the imaging system 100, PACS, RIS, CIS, and/or HIS can be combined into a single integrated system for easier storing, organizing, searching, correlating, and analysis of data.

FIG. 1B illustrates an example data transfer sequence (e.g., a sequence of communication and data transfers) that can be implemented in the example medical imaging system 100 of FIG. 1A. According to the illustrated example, the acquisition workstation 120 requests images from the imaging modality 110 at 150. As a result, the acquisition workstation 120 is provided with at least one image from the imaging modality 110 at 152 which, in turn, is forwarded from the acquisition workstation 120 to the image processing system 130 at 154.

At 156, the image viewer 140 makes a request to view the aforementioned image. As a result, the image is provided to the image processing system 130 at 158 and to the image viewer 140 at 160.

According to the illustrated example, user activity (e.g., commands, and/or image arrangements) are logged or recorded and provided to the image processing system 130 at 162. In some examples, the user activity is also forwarded to the acquisition workstation 120 and the imaging modality 130 at 164. In this example, the acquisition workstation 120 generates, via a learning network associated with a learning process, a user interface configuration based on the user activity in relationship to a context of medical content data (e.g., medical case data, medical case history, medical metadata, etc.) and forwards the generated user interface configuration to the image processing server 130 at 170. In other examples, the image processing server 130 generates the user interface configuration. As will be discussed in greater detail below in connection with FIGS. 2-13, the user interface configuration is generated or adapted based on machine learning techniques (e.g., deep learning techniques) of the user's (or multiple users) manipulation of a viewing interface and/or the user's manipulation of images in relationship to the aforementioned context (subsequent to an initial hang being presented). The generated user interface configuration is then forwarded to the imaging processing system 130 at 170.

In this example, the image viewer 140 sends a request to the image processing server 130 for an additional image at 172. As a result, a user interface of the image viewer 140 is updated based on the generated user interface configuration. Images from the image acquisition workstation 120 are forwarded to the image viewer 140 via the image processing system 130 at 176, 178. In other words, the later forwarded image is viewed with the updated user interface at 174 in this example. According to the illustrated example of FIG. 1B, an arrow 180 indicates how the learning process in examples disclosed herein can be repeated to (continuously and/or periodically) refine and/or adapt user interface models based on the recorded user input.

Figure 2:
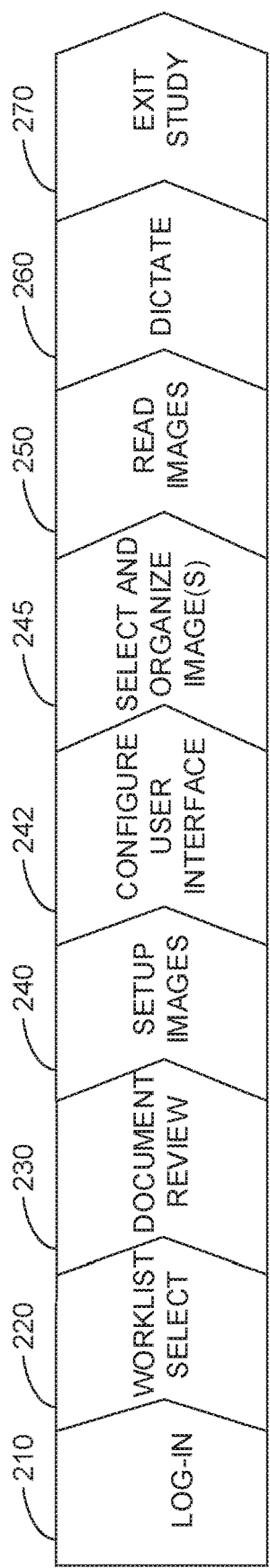
FIG. 2 illustrates an example radiology workflow in which examples disclosed herein can be implemented.

FIG. 2 illustrates an example radiology workflow in which examples disclosed herein can be implemented. A radiologist logs into an imaging system (block 210), reviews his/her worklist (block 220), and selects a study to review (block 230). In some medical imaging systems, imaging data is opened in an initial setup (block 240). Further, a reviewing physician configures settings, interface items (e.g., interface buttons, etc.) (block 242) and selects and organized images (block 245), depending on a type of case he/she is reviewing (block 250). During or after image reading (block 250), the reviewing physician can dictate findings, notes, instructions, etc. (block 260), and then exit the study (block 270).

According to some known examples, the reviewing physician will sometimes re-adjust images (e.g., zoom, pan and/or reorder the images) and/or adjust a user interface based on individual preferences. In such known examples, often the reviewing physician will need to manually set the user interface preferences and move and/or select images according to his/her preferences. The adjustment of the user interface can be time consuming and also computationally intensive.

Examples disclosed herein utilize training data to develop models used to predict preferences, sequences and/or image organization to save time and/or effort on the part of the reviewing physician or other practitioner. In particular, examples disclosed herein use machine learning to adapt a user interface based on a context of medical contend data to enable more efficient utilization of image data, thereby saving time and costs associated with time wasted configuring a user interface. Examples disclosed herein also enable more efficient utilization of processor/computing resources by streamlining user experiences. In particular, some examples disclosed herein can reduce processing associated with reconfiguring a user interface by caching predicted interface adjustments or images, or enabling streamlined data transfers based on predicted user commands (e.g., predicted based on learning techniques).

Figure 3:
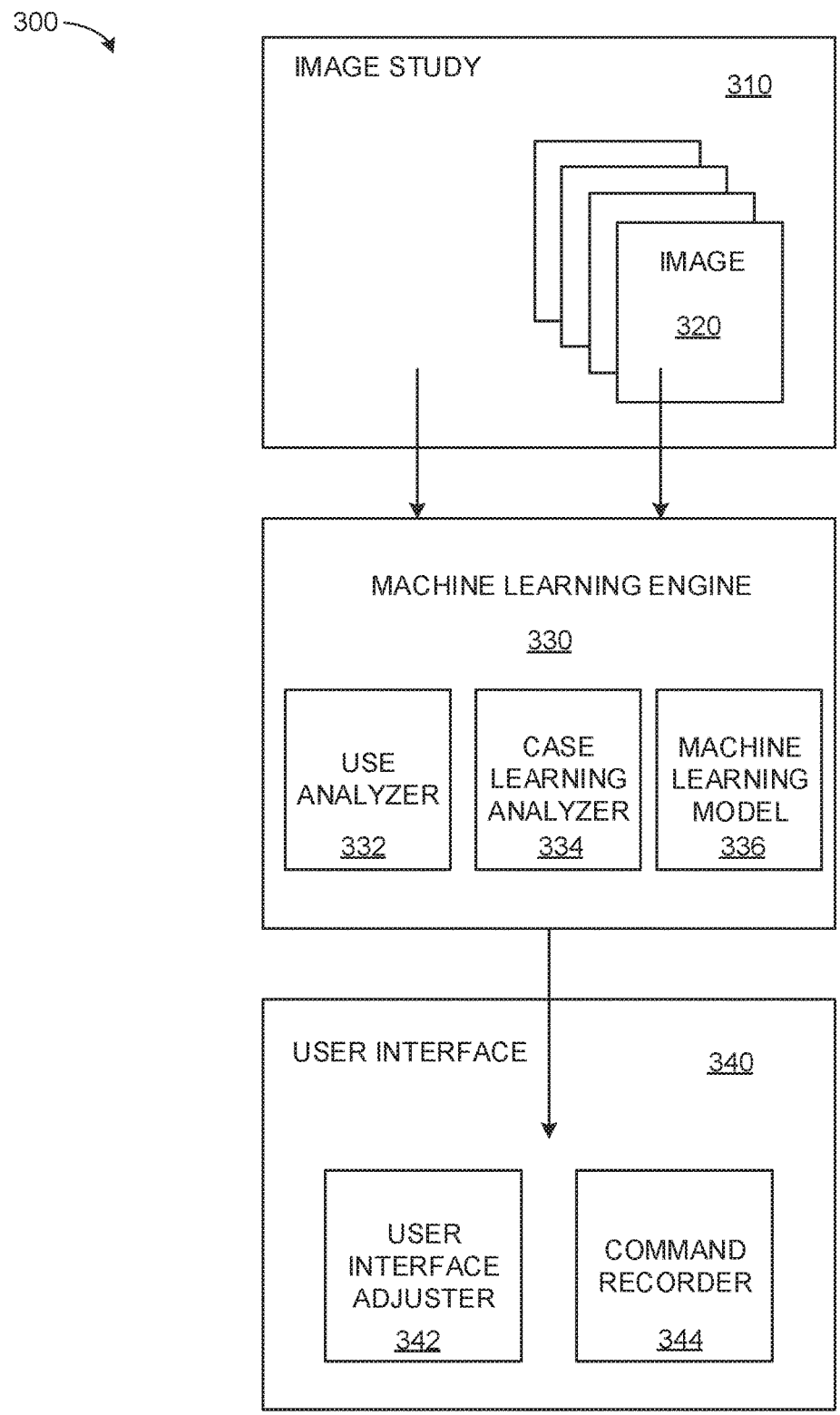
FIG. 3 depicts an example learning system to adjust a user interface of a medical imaging device in accordance with teachings of this disclosure.

FIG. 3 depicts an example of a learning system 300 to adjust a user interface based on learning (e.g., deep learning techniques) in accordance with teachings of this disclosure. The example learning system 300 of the illustrated example includes an image study 310 including study information, one or more individual images 320 including image DICOM header information, a machine learning engine 330 that includes a use analyzer (e.g., a use monitor) 332, a case learning analyzer (e.g., a medical content data analyzer) 334, and a machine learning model (e.g., an artificial neural network) 336. The example learning system 300 also includes a user interface 340 with a user interface adjuster 342 and a command recorder 344. The components of the learning system 300 can be implemented in software, hardware, and/or firmware, for example.

In operation, the study 310 information and individual image 320 information are extracted from an image study and provided or otherwise made accessible to the machine learning engine 330. Based on user input and user commands (e.g., a sequence of multiple user commands), the machine learning engine 330 generates a configuration of the user interface 340 (e.g., a configuration generated by the user interface adjuster 342). For example, an artificial neural network and/or other adaptive processing model can be used by the machine learning engine 330 to select or generate a user interface configuration based on commands and/or user input recorded by the command recorder 344. In some examples, the medical content data can include case data, case histories, case study information, diagnoses, medical report information, case metadata, case terms, etc.

To analyze user commands and/or monitored user actions, the use analyzer 332 analyzes user inputs representing actions performed during viewing of images at a clinical display. In other words, the use analyzer 332 develops and/or trains models based on monitored user actions.

According to the illustrated example, the case learning analyzer 334 is used to analyze and/or determine a context of medical content data. For example, the case learning analyzer 334 develops training data and/or models associated with metadata or case histories of medical cases. The case learning analyzer 334 can utilize key terms, image content, diagnoses, image classifications and/or individual case histories. In some examples, the case learning analyzer 334 performs a similarity analysis by analyzing similarities between images of different medical cases (e.g., in conjunction with user commands or inputs).

In some examples, the machine learning engine 330 implements a machine learning model 336, which is an artificial neural network and/or other machine or deep learning construct to determine or generate a user interface configuration. In some examples, context based algorithms can use DICOM header elements to associate medical content data with user input. In some examples, as the user issues various input commands over time, the artificial neural network nodes are updated by the machine learning model 336, and the nodes continue to evolve. Although artificial neural networks are discussed above, other forms of artificial intelligence, such as fuzzy logic, Boltzmann machine, Bayesian network, etc., can be used as machine learning techniques to determine an applicable user input configuration.

The machine learning engine 330 and/or the machine learning model 336 is used to analyze image similarities between different medical cases so that images and/or their associated data can be correlated to user inputs so that subsequently encountered similar images can be correlated or tied to the user inputs. By correlating images with user input, application settings and/or user interface configuration settings, the machine learning model 336 learns a context that matches and/or correlates the user input/commands with the content of the images, which can include associated data and/or metadata. In other words, the example machine learning model 336 determines patterns (e.g., contextual patterns) between a context/situation and resulting user interface application configurations (e.g., interface configuration changes) that have been applied by a user. As an example, instead of simply correlating a situation to a user interface configuration, the machine learning model 336 can determine similarities in situations (e.g., similarities in context and/or images, etc.) and/or a degree of similarity without necessarily requiring an exact situation, thereby resulting in great adaptability in learning and application of the modified user interface configurations. Additionally or alternatively, in some examples, the application is executed is modified or adjusted (e.g., a sequence of hierarchy of when different modules or executables are run, etc.) by the machine learning model 336.

Figure 4:
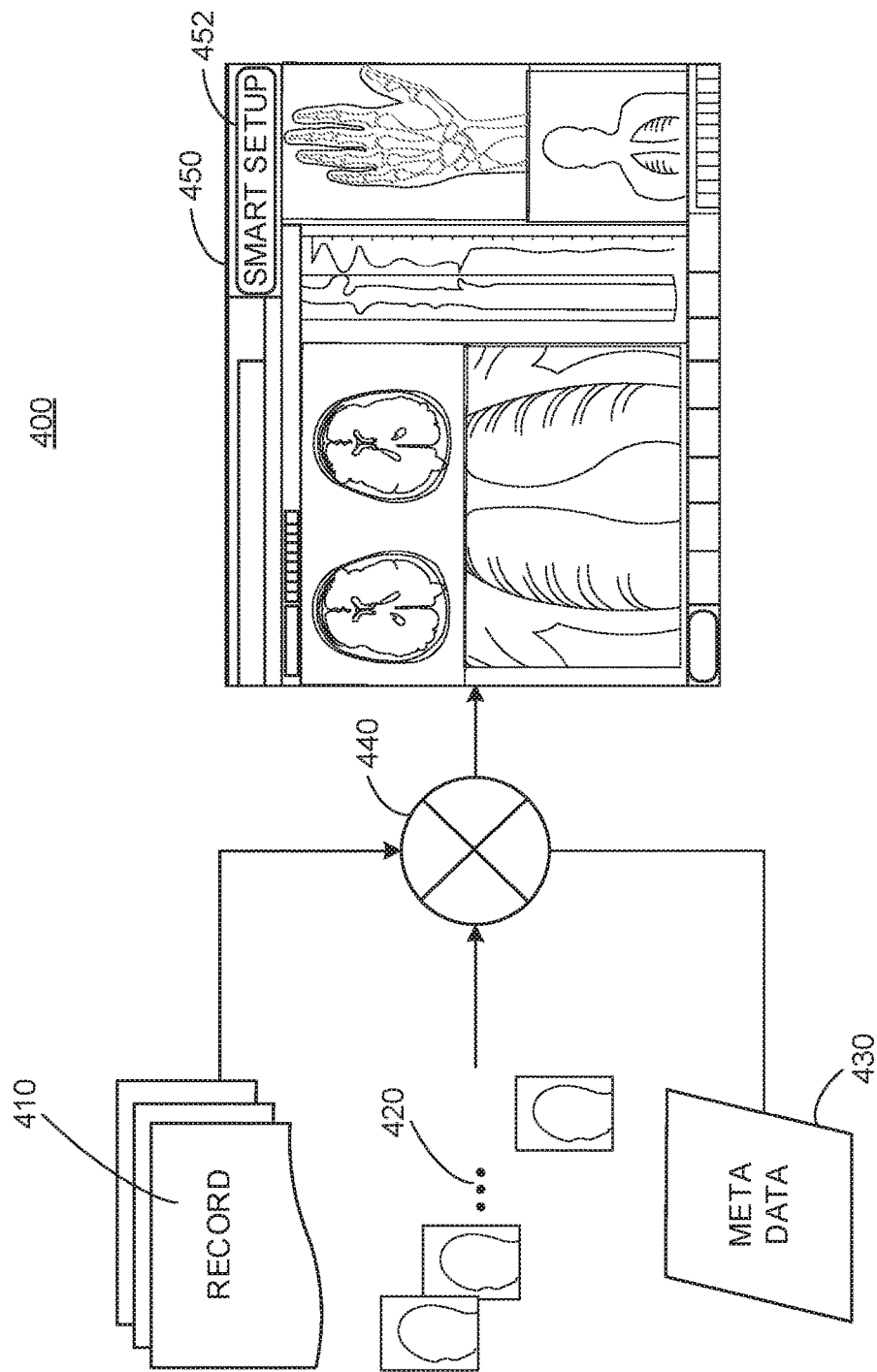
FIG. 4 provides an example visualization of image data information that may be analyzed in examples disclosed herein.

FIG. 4 provides an example visualization of image data information 400 that can be analyzed in examples disclosed herein. According to the illustrated example, records (e.g., medical records) 410 are associated with medical images 420. As can also be seen in the example of FIG. 4, metadata 430 is associated with the records 410 and/or the images 420. According to the illustrated example of FIG. 4, a user configuration mapper 440 displays a user interface (e.g., a user display) 450 based on learned user interface configuration data developed by the machine learning engine 330.

Examples disclosed herein can generate and/or modify a user interface and/or other application configuration by utilizing learning based on context of any of the records 410 or the images 420 in combination with recorded user actions and/or commands. In particular, learning techniques, such as those described below in connection with FIGS. 5-12, can be implemented to develop user interface training models based on a context of the images 420, the records 410 and/or the metadata 430 in relationship to the recorded user actions, clinical context, observed results, etc. For example, contextual patterns, which can be used to associate different or similar situations encountered, can be learned based on the user inputs in reference to contextual information. In some examples, the user interface 450 is provided with an icon or symbol 452 to represent a user interface configuration (e.g., a batched command, rearranged menu items or icons, shifted or rearranged menu item hierarchies, etc.).

Figure 5:
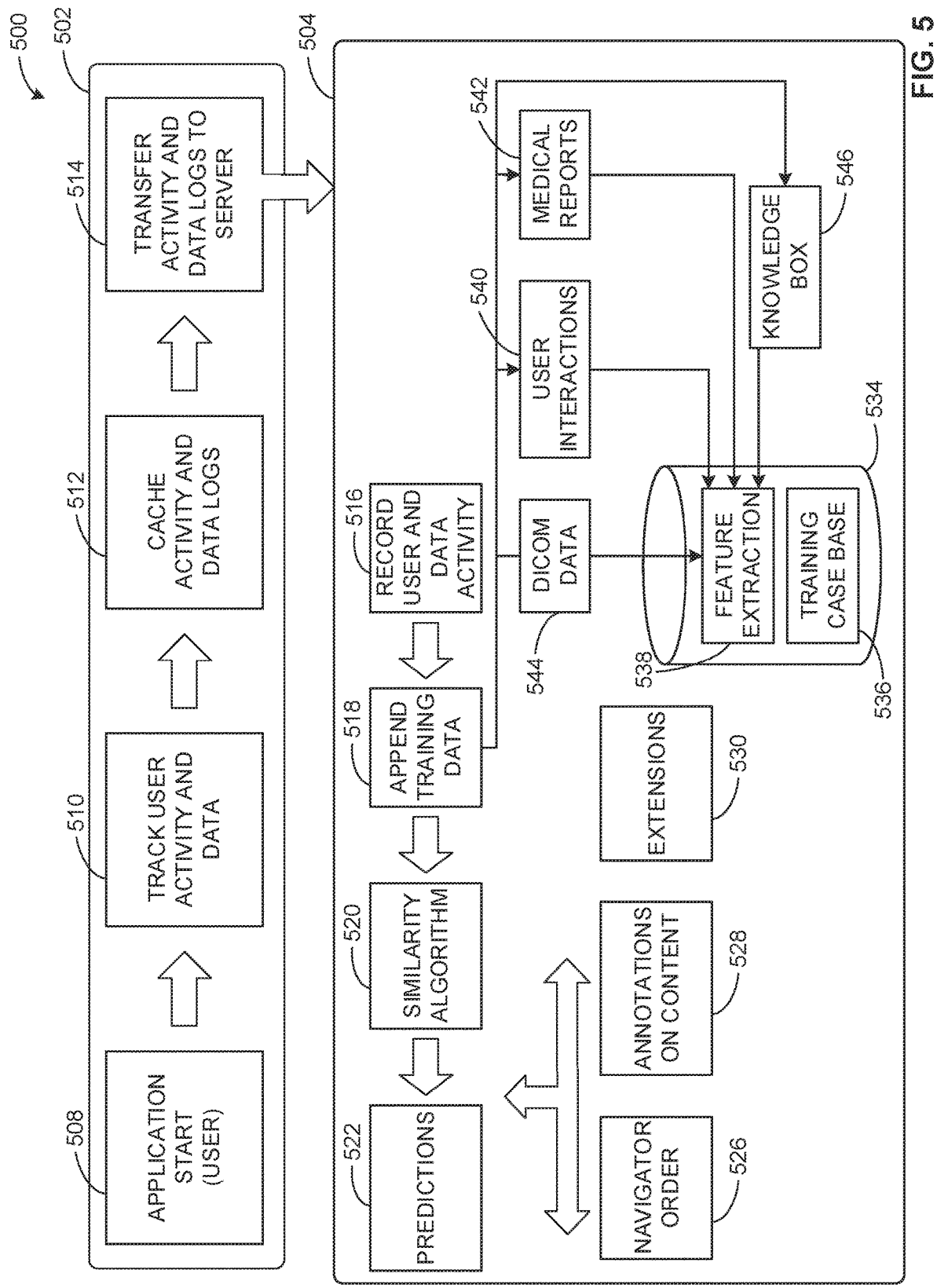
FIG. 5 depicts a high level data flow for an example machine learning algorithm.

FIG. 5 depicts a high level data flow 500 for an example machine learning algorithm to generate a user interface configuration. The high level data flow can be implemented by the machine learning engine 300 and/or the machine learning model 336. In this example, the high level data flow 500 is used to develop predictions (e.g., user computer behavior models, interface use models, application modification predictions, etc.) so that a user interface configuration can be generated or modified to better suit practitioner viewing needs. In particular, the user interface configuration can be adapted for more time-efficient use by avoiding common user interface setup steps and/or image arrangements. According to the illustrated example of FIG. 5, steps 502 represent activities that can be performed on the image viewer 140 while steps 504 represent server-based activities (e.g., the image processing server 130, for example).

At block 508, a user (e.g., a reviewing physician) starts work on an application associated with an image viewer 140 by opening a study on the image viewer 140. In this example, the user activity (e.g., commands, sequences, inputs, image arrangement, etc.) are tracked or recorded at block 510. Further, the user activity is cached into data logs at block 512. In this example, the user activity and data logs are cached and transferred to a server (e.g., the image processing server 130 and/or the data acquisition workstation 120) (block 514).

At block 516, user and data are recorded and/or forwarded to the image processing server 130 and/or the data acquisition workstation 120. In some examples, data and/or metadata related to medical content data is also forwarded along with the user data. In this example, the aforementioned user and data activity are used to append training data at block 518. In other words, the training data is utilized so that the machine learning engine 330 can develop or modify (e.g., refine) user interface configuration(s).

The machine learning engine 330 of the illustrated example executes a similarity algorithm 520 of the appended training data to develop predictions 522. According to the illustrated example, user commands are analyzed in conjunction with medical content data and/or its associated metadata to develop the predictions 522. In this example, the predictions 522 are refined and/or modified as the aforementioned training data is appended or corrected.

In some examples, the similarity algorithm 520 utilizes a similarity-based classification model to estimate a class label of an incoming study based on a degree of similarity between the incoming data and a set of training data samples and/or pairwise similarities between the training samples. Accordingly, similarity calculation can be done based on feature vectors extracted from training data and an incoming study. For example, a similarity score is calculated by a summation of Euclidian distance measurement(s) of individual features. In some such examples, the nearest neighbors are calculated and recommended to the users using a learning and/or analytics engine. For example, a Euclidian distance measurement on a high dimensional space can be calculated using equation 1 below, where Xi and Yi represent numeric quantifications of individual feature vectors in n dimensional space:

$$D = \text{Sqrt}(\Sigma_{i=0}^{n}(Xi-Yi)^2) \tag{1}$$

In this example, a minimal distance value directly translates to higher similarity. For features with string values, comparisons done and appropriate numeric value weightage is associated for exact match and approximate match to be later used for a similarity calculation.

As a result of developing the predictions 522, a user interface configuration and/or a user interface displaced on the image viewer 140 is adjusted. In particular, any of a navigation order 526, annotations on content 528, or extensions (e.g., extensions to menu icons and/or shortcuts on a user interface, etc.) 530 can be adjusted based on the predictions 522.

In some examples, training data is stored on a training data storage 534. The example training data storage 534 includes a training case base 536 and feature extraction data 538. In this example, at least one of user interactions (e.g., user commands, user input sequences, user rearrangement of elements of a user interface, etc.) 540, medical reports data 542, DICOM data 544 or knowledge data (e.g., knowledge base data, anatomy data, physiology data, etc.) 546 are incorporated into training data associated with machine learning and stored in the training data storage 534. In some examples, the training data is developed for a later session (e.g., user commands/inputs in the context of content data are learned in a first reading session and then a user interface is adjusted prior or during a second reading session that is subsequent to the first session). In some other examples, the training data is updated during a session.

Figure 6:
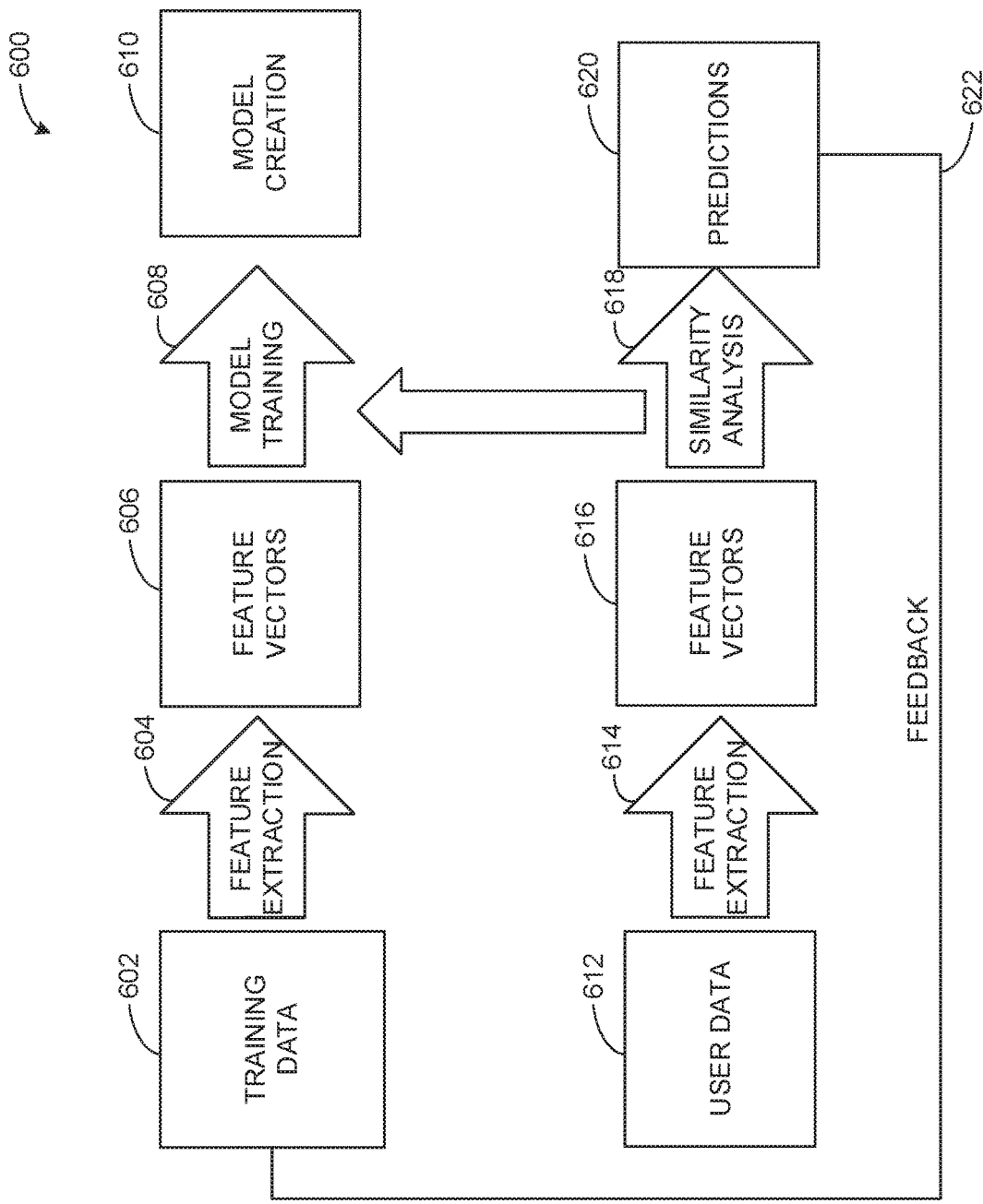
FIG. 6 depicts a high level data flow of an example model learning and prediction algorithm.

FIG. 6 depicts a high level data flow of an example model learning and prediction algorithm 600. The example of FIG. 6 illustrates a data flow in which training and model data is updated, corrected and/or appended based on machine learning performed by the machine learning engine 330 of FIG. 3. In this example, the machine learning engine 330 generates, modifies and/or appends training data 602. In particular, the machine learning engine 330 extracts features 604 to define feature vectors 606. In turn, the feature vectors 606 are utilized in a model training process 608 to define a model 610.

In this example, user data 612 undergoes feature extraction 614 to define feature vectors 616. To develop the model 610, the feature vectors 606 are compared to the feature vectors 616 in a similarity analysis 618, thereby generating predictions 622. In this example, the predictions 622 provide feedback 622 to the training data 602. In other words, the predictions 622 are used to refine, improve and/or augment the training data 602 in this example. In some examples, vectors associated with a single user are extracted. In such examples, the vectors can be used to generate a model tailored to an individual (e.g., individual preferences). Additionally or alternatively, vectors associated with multiple users are utilized to develop a model for multiple users. In some such examples, the vectors based on multiple users are used to generate a user interface configuration (e.g., an aggregate user interface configuration) that is forwarded to multiple ones of the display viewers 140.

While an example manner of implementing the example learning system 300 of FIG. 3 is illustrated in FIG. 3, one or more of the elements, processes and/or devices illustrated in FIG. 3 may be combined, divided, re-arranged, omitted, eliminated and/or implemented in any other way. Further, the example machine learning engine 330, the example use analyzer 332, the example case learning analyzer 334, the machine learning model 336, the example user interface 340, the example user interface adjuster 340, the example command recorder 344 and/or, more generally, the example learning system 300 of FIG. 3 may be implemented by hardware, software, firmware and/or any combination of hardware, software and/or firmware. Thus, for example, any of the example machine learning engine 330, the example use analyzer 332, the example case learning analyzer 334, the machine learning model 336, the example user interface 340, the example user interface adjuster 340, the example user interface adjuster 342, the example command recorder 344 and/or, more generally, the example learning system 300 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example machine learning engine 330, the example use analyzer 332, the example case learning analyzer 334, the machine learning model 336, the example user interface 340, the example user interface adjuster 340, the example user interface adjuster 342 and/or the example the example command recorder 344 is/are hereby expressly defined to include a non-transitory computer readable storage device or storage disk such as a memory, a digital versatile disk (DVD), a compact disk (CD), a Blu-ray disk, etc. including the software and/or firmware. Further still, the example learning system 300 of FIG. 3 may include one or more elements, processes and/or devices in addition to, or instead of, those illustrated in FIG. 3, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 7:
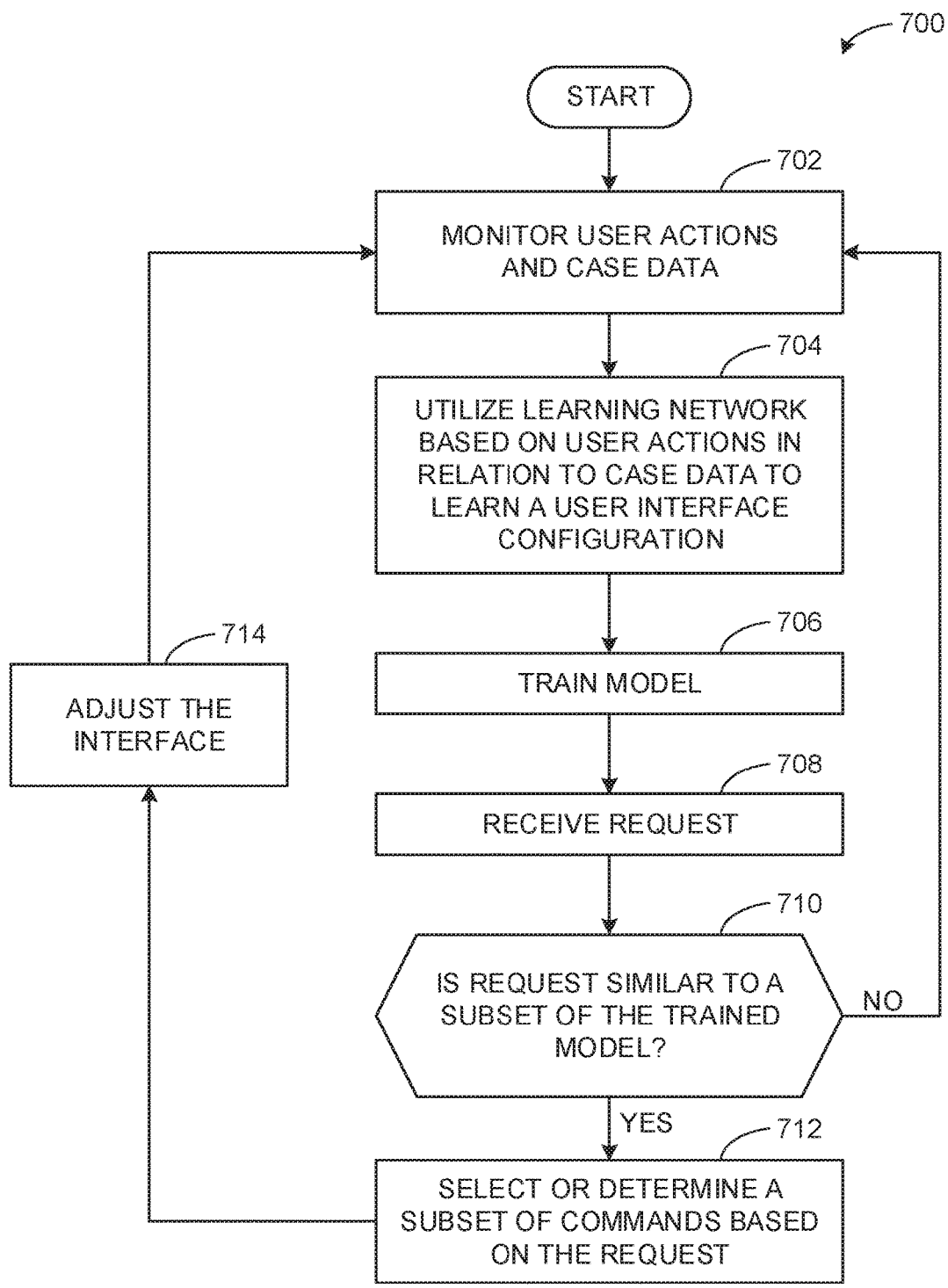
FIG. 7 is a flowchart representative of machine readable instructions which may be executed to implement the example system 300 of FIG. 3.
Figure 8:
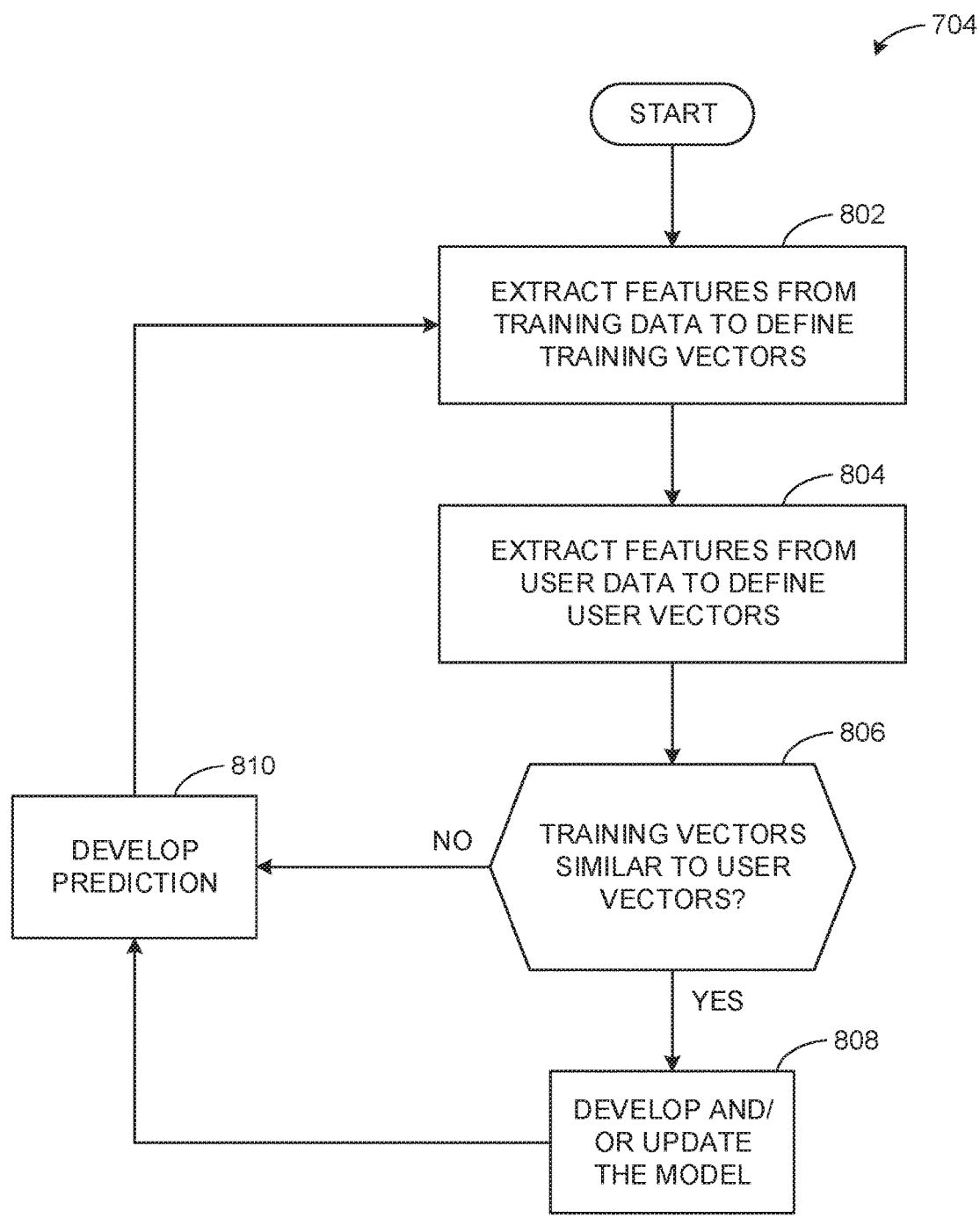
FIG. 8 is a flowchart of an example subroutine of the machine readable instructions of FIG. 7.

Flowcharts representative of example hardware logic, machine readable instructions, hardware implemented state machines, and/or any combination thereof for implementing the learning system 300 of FIG. 3 are shown in FIGS. 7 and 8. The machine readable instructions may be an executable program or portion of an executable program for execution by a computer processor such as the processor 1312 shown in the example processor platform 1300 discussed below in connection with FIG. 13. The program may be embodied in software stored on a non-transitory computer readable storage medium such as a CD-ROM, a floppy disk, a hard drive, a DVD, a Blu-ray disk, or a memory associated with the processor 1312, but the entire program and/or parts thereof could alternatively be executed by a device other than the processor 1312 and/or embodied in firmware or dedicated hardware. Further, although the example programs described with reference to the flowcharts illustrated in FIGS. 7 and 8, many other methods of implementing the example learning system 300 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 7 and 8 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C.

An example method 700 of FIG. 7 begins as a user (e.g., a reviewing physician) is to utilize a medical imaging interface. In this example, the user will access images during multiple sessions (e.g., multiple sessions defining different medical cases) on the image viewer 140.

According to the illustrated example, the command recorder 344 monitors user actions and case data (block 702). In this example, the user actions (e.g., commands, settings, image manipulation) are monitored in conjunction with medical content data.

The machine learning engine 330 utilizes a learning network to learn a user interface configuration based on the user actions in relationship to content of the medical content data (e.g., based on monitored user actions in relationship to a context of the medical content data) (block 704). In some examples, case metadata is also analyzed. Additionally or alternatively, image data (e.g., image similarity data) is utilized by the machine learning engine 330 to learn the user configuration.

In this example, the model is trained by the use analyzer 332, the machine learning model 336 and/or the case learning analyzer 334 (block 706). In particular, feature vectors associated with a training module as well feature vectors associated with user input data are utilized to train the model.

Next, in some examples, a request is received from a user (block 708). In particular, the request can include information of a new incoming medical case to be viewed and/or specifically requested parameters provided from a user.

In some examples, the request is compared to a subset of the trained model for similarity (block 710). If the request is not similar to the subset (e.g., the trained model does not have a relevant user interface configuration based on the request), control of the process proceeds to block 702. Otherwise, control of the process proceeds to block 712.

At block 712, the user interface adjuster 342 selects or determines a subset of commands from the trained model based on the request. In particular, the example user interface adjuster 342 defines a group of commands and/or user interface adjustments from the trained model based on the request. In other words, the user interface adjuster 342 provides a user interface configuration based on the request being similar to at least one subset of the trained model.

At block 714, the user interface adjuster 342 adjusts and/or modifies a user interface of the image viewer 140 (e.g., applies the user interface configuration to the image viewer 140) and control of the process returns to block 702. In some examples, menu items of a user interface are adjusted. Additionally or alternatively, an icon, symbol or button representing a learned command or set of commands is shown on the image viewer 140.

Turning to FIG. 8, a flowchart representative of the example subroutine 704 of FIG. 7 is shown. The example subroutine 704 begins as features are extracted from training data to define training vectors by the user analyzer 332, the machine learning model 336 and/or the case learning analyzer 334 (block 802).

According to the illustrated example, features are extracted from user data to define user vectors by the user analyzer 334 and/or the machine learning model 336 (block 804). For example, the features can be related to translation, zooming, panning or annotations of medical case images.

It is then determined if the training vectors are similar to the user vectors (block 806). In particular, a degree of similarity between the training vectors and the user vectors is determined. If the training vectors are similar to the user vectors based on the degree of similarity (block 806), control of the process proceeds to block 808. Otherwise, control of the process proceeds to block 810.

At block 808, the model is developed and/or updated by the machine learning engine 330. For example, a pre-defined condition (e.g., a case history or potential diagnosis) can be linked a user interface configuration.

At block 810, a prediction is developed and/or updated. In this example, the prediction developed and/or updated based on the comparison of the training vectors to the user vectors. Subsequently, control of the process returns to block 802.

Figure 9:
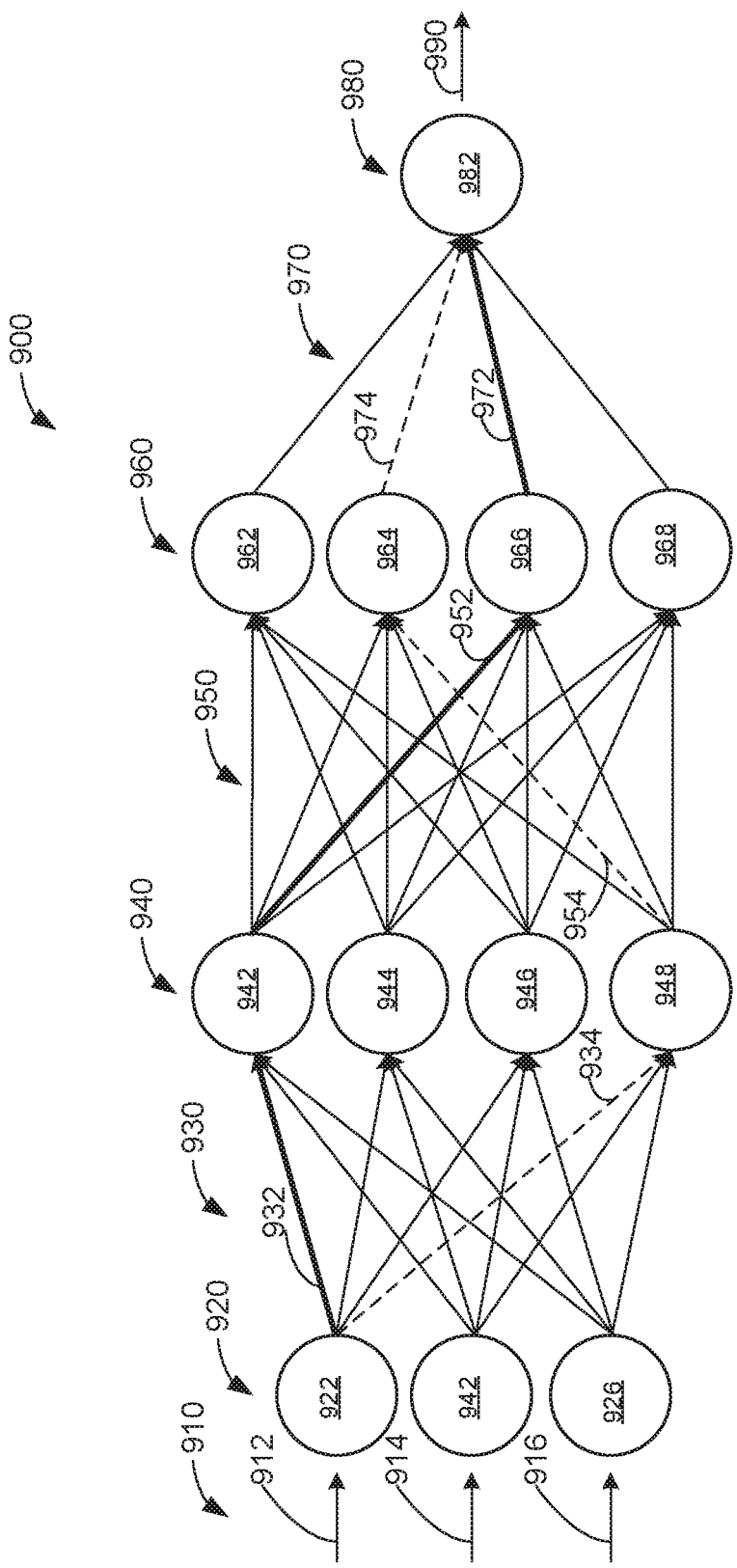
FIG. 9 is a representation of an example deep learning neural network that can be implemented in examples disclosed herein.

FIGS. 9-12 illustrate example learning techniques and methods that can be implemented in examples disclosed herein. The examples of FIGS. 9-12 can be implemented by the machine learning model 336, for example, to create a user interface model that associated user interactions with user identifications, data context and/or data content (e.g., case information). In particular, the examples of FIGS. 9-12 can be implemented to learn a user interface in the context of user patterns, user preferences, individual preferences, image similarity, case histories, case types, metadata, etc. FIG. 9 is a representation of an example deep learning neural network 900 that can be implemented in examples disclosed herein. The example neural network 900 includes layers 920, 940, 960, and 980. The layers 920 and 940 are connected with neural connections 930. The layers 940 and 960 are connected with neural connections 950. The layers 960 and 980 are connected with neural connections 970. Data flows forward via inputs 912, 914, 916 from the input layer 920 to the output layer 980 and to an output 990.

The layer 920 is an input layer that, in the example of FIG. 9, includes a plurality of nodes 922, 924, 926. The layers 940 and 960 are hidden layers and include, the example of FIG. 9, nodes 942, 944, 946, 948, 962, 964, 966, 968. The neural network 900 can include more or less hidden layers 940 and 160 than shown. The layer 980 is an output layer and includes, in the example of FIG. 9, a node 982 with an output 990. Each input 912-916 corresponds to a node 922-126 of the input layer 920, and each node 922-926 of the input layer 920 has a connection 930 to each node 942-948 of the hidden layer 940. Each node 942-948 of the hidden layer 940 has a connection 950 to each node 962-968 of the hidden layer 960. Each node 962-968 of the hidden layer 960 has a connection 970 to the output layer 980. The output layer 980 has an output 990 to provide an output from the example neural network 900.

Of connections 930, 950, and 970 certain example connections 932, 952, 972 can be given added weight while other example connections 934, 954, 974 are given less weight in the neural network 900. Input nodes 922-926 are activated through receipt of input data via inputs 912-916, for example. Nodes 942-948 and 962-968 of hidden layers 940 and 960 are activated through the forward flow of data through the network 900 via the connections 930 and 950, respectively. Node 982 of the output layer 980 is activated after data processed in hidden layers 940 and 960 is sent via connections 970. When the output node 982 of the output layer 980 is activated, the node 982 outputs an appropriate value based on processing accomplished in hidden layers 940 and 160 of the neural network 900.

Figure 10:
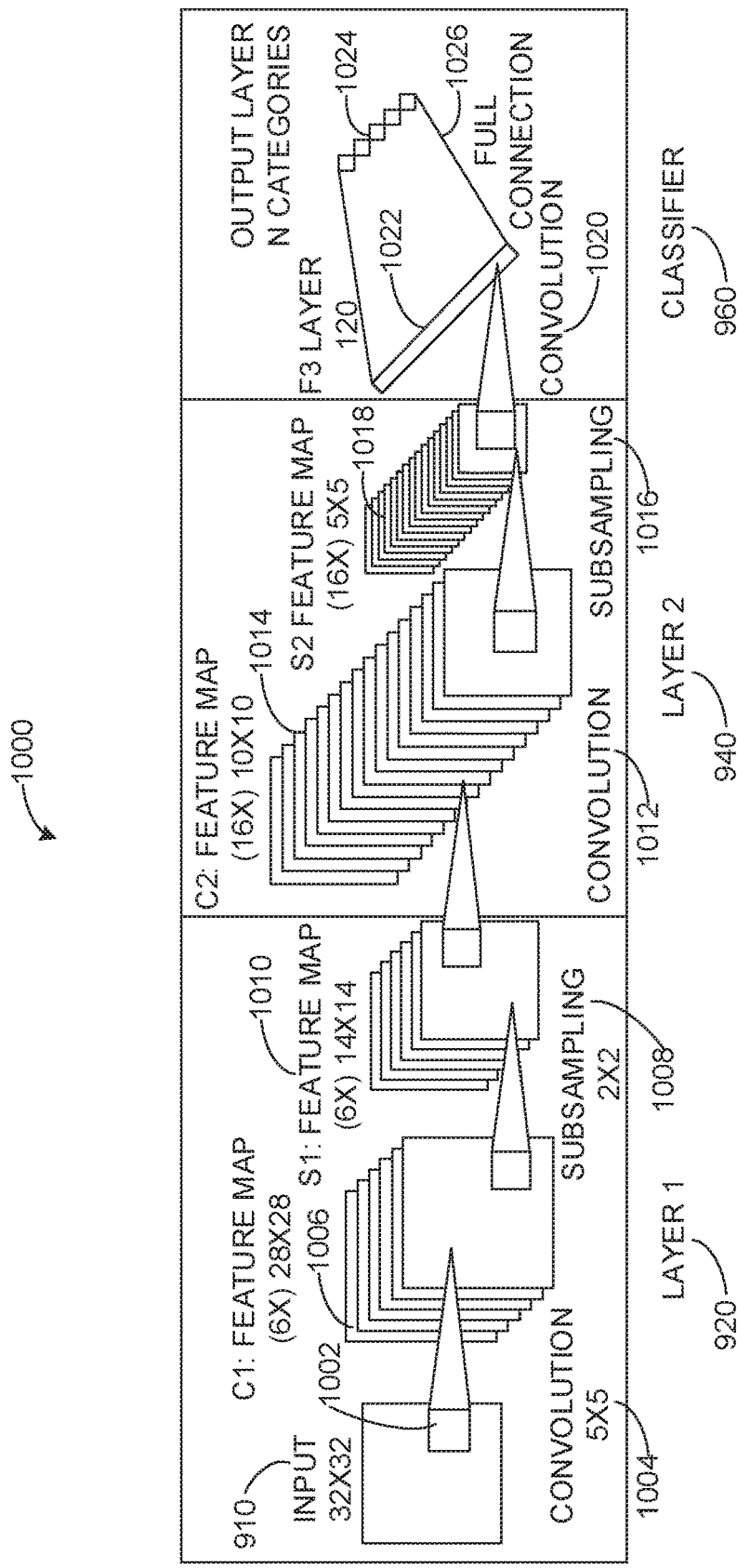
FIG. 10 illustrates a particular implementation of the example neural network of FIG. 9 as a convolutional neural network.

FIG. 10 illustrates a particular implementation of the example neural network 900 as a convolutional neural network 1000. As shown in the example of FIG. 10, an input 910 is provided to the first layer 920 which processes and propagates the input 910 to the second layer 940. The input 910 is further processed in the second layer 940 and propagated to the third layer 960. The third layer 960 categorizes data to be provided to the output layer 980. More specifically, as shown in the example of FIG. 10, a convolution 1004 (e.g., a 5×5 convolution, etc.) is applied to a portion or window (also referred to as a "receptive field") 1002 of the input 910 (e.g., a 32×32 data input, etc.) in the first layer 920 to provide a feature map 1006 (e.g., a (6×) 28×28 feature map, etc.). The convolution 1004 maps the elements from the input 910 to the feature map 1006. The first layer 920 also provides subsampling (e.g., 2×2 subsampling, etc.) to generate a reduced feature map 1010 (e.g., a (6×) 14×14 feature map, etc.). The feature map 1010 undergoes a convolution 1012 and is propagated from the first layer 920 to the second layer 940, where the feature map 1010 becomes an expanded feature map 1014 (e.g., a (16×) 10×10 feature map, etc.). After subsampling 1016 in the second layer 940, the feature map 1014 becomes a reduced feature map 1018 (e.g., a (16×) 4×5 feature map, etc.). The feature map 1018 undergoes a convolution 1020 and is propagated to the third layer 960, where the feature map 1018 becomes a classification layer 1022 forming an output layer of N categories 1024 with connection 1026 to the convoluted layer 1022, for example.

Figure 11:
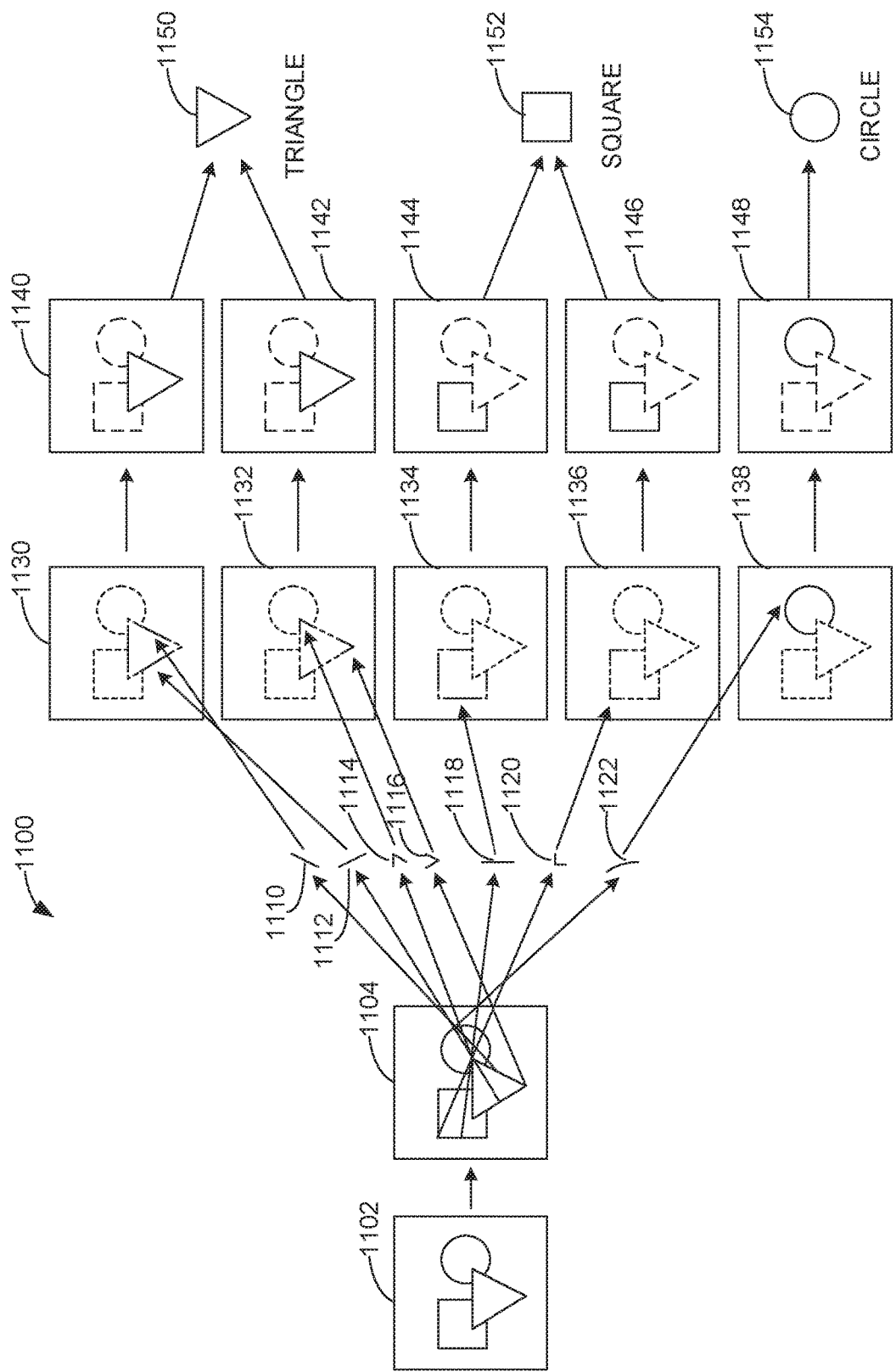
FIG. 11 is a representation of an example image analysis convolutional neural network that can be implemented in examples disclosed herein.

FIG. 11 is a representation of an example image analysis convolutional neural network 1100 that can be implemented in examples disclosed herein. In particular, the example image analysis of FIG. 11 can be implemented to analyze similarities in medical images between cases (e.g., to develop training models based on medical case images). The convolutional neural network 1100 receives an input image 1102 and abstracts the image in a convolution layer 1104 to identify learned features 1110-1122. In a second convolution layer 1130, the image is transformed into a plurality of images 1130-1138 in which the learned features 1110-1122 are each accentuated in a respective sub-image 1130-1138. The images 1130-1138 are further processed to focus on the features of interest 1110-1122 in images 1140-1148. The resulting images 1140-1148 are then processed through a pooling layer which reduces the size of the images 1140-1148 to isolate portions 1150-1154 of the images 1140-1148 including the features of interest 1110-1122. Outputs 1150-1154 of the convolutional neural network 1100 receive values from the last non-output layer and classify the image based on the data received from the last non-output layer. In certain examples, the convolutional neural network 1100 can contain many different variations of convolution layers, pooling layers, learned features, and outputs, etc.

Figure 12:
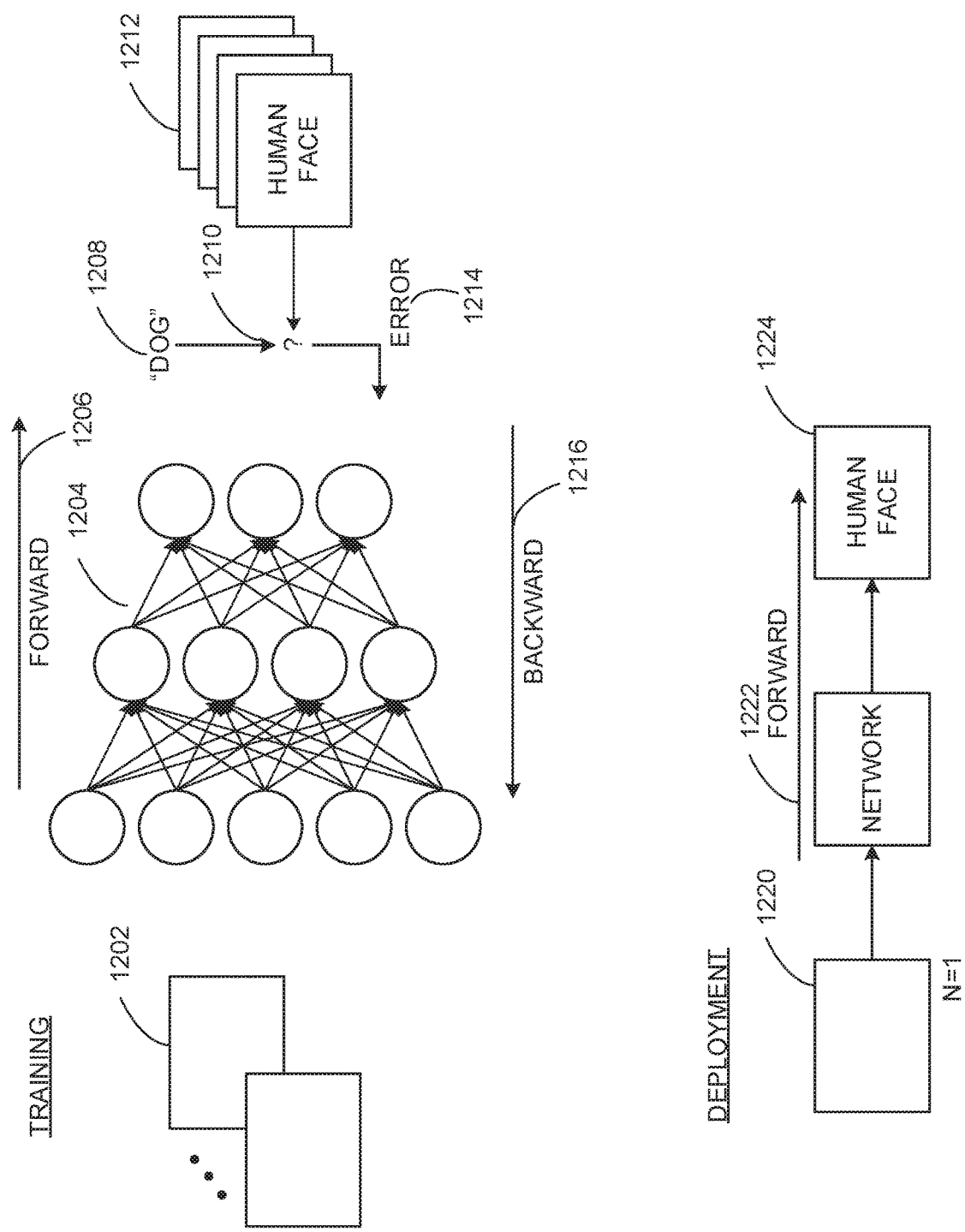
FIG. 12 illustrates example training and deployment phases of a deep learning network.

FIG. 12 illustrates example training and deployment phases of a deep learning network that can be implemented in examples disclosed herein. As shown in the example of FIG. 12, in the training phase, a set of inputs 1202 is provided to a network 1204 for processing. In this example, the set of inputs 1202 can include facial features of an image to be identified. The network 1204 processes the input 1202 in a forward direction 1206 to associate data elements and identify patterns. The network 1204 determines that the input 1202 represents a dog 1208. In training, the network result 1208 is compared 1210 to a known outcome 1212. In this example, the known outcome 1212 is a human face (e.g., the input data set 1202 represents a human face, not a dog face). Since the determination 1208 of the network 1204 does not match 1210 the known outcome 1212, an error 1214 is generated. The error 1214 triggers an analysis of the known outcome 1212 and associated data 1202 in reverse along a backward pass 1216 through the network 1204. Thus, the training network 1204 learns from forward 1206 and backward 1216 passes with data 1202, 1212 through a communication network.

Once the comparison of network output 1208 to known output 1212 matches 1210 according to a certain criterion or threshold (e.g., matches n times, matches greater than x percent, etc.), the training network 1204 can be used to generate a network for deployment with an external system. Once deployed, a single input 1220 is provided to a deployed deep learning network 1222 to generate an output 1224. In this case, based on the training network 1204, the deployed network 1222 determines that the input 1220 is an image of a human face 1224.

Accordingly, an analysis similar to the face example shown in FIG. 12 can be performed with respect to medical images in examples disclosed herein. For example, multiple images associated with different cases can be analyzed or learned, via machine learning processes, for similarity in conjunction with medical data (e.g., medical history information, diagnoses, metadata, key words, etc.) to develop a context associated with user inputs/commands to adapt a user interface configuration.

In some examples, DICOM metadata (e.g., a DICOM header) analysis leverages medical content metadata to do an approximate fuzzy match between clinical images rather than a literal pixel-by-pixel (2D) or voxel-by-voxel (3D) or literal image content match. In some examples, learning is transferred to apply lessons learned in one domain to another domain.

Additionally or alternatively, labels, indicators, identification numbers, etc., are extracted from DICOM headers associated with images and other clinical content. As a result, the images and clinical content are matched based on an assumption from the DICOM header content. In particular, it can be assumed that because headers have similar words, indicators, labels, etc., two or more items (or any appropriate number of items) have a relationship.

Figure 13:
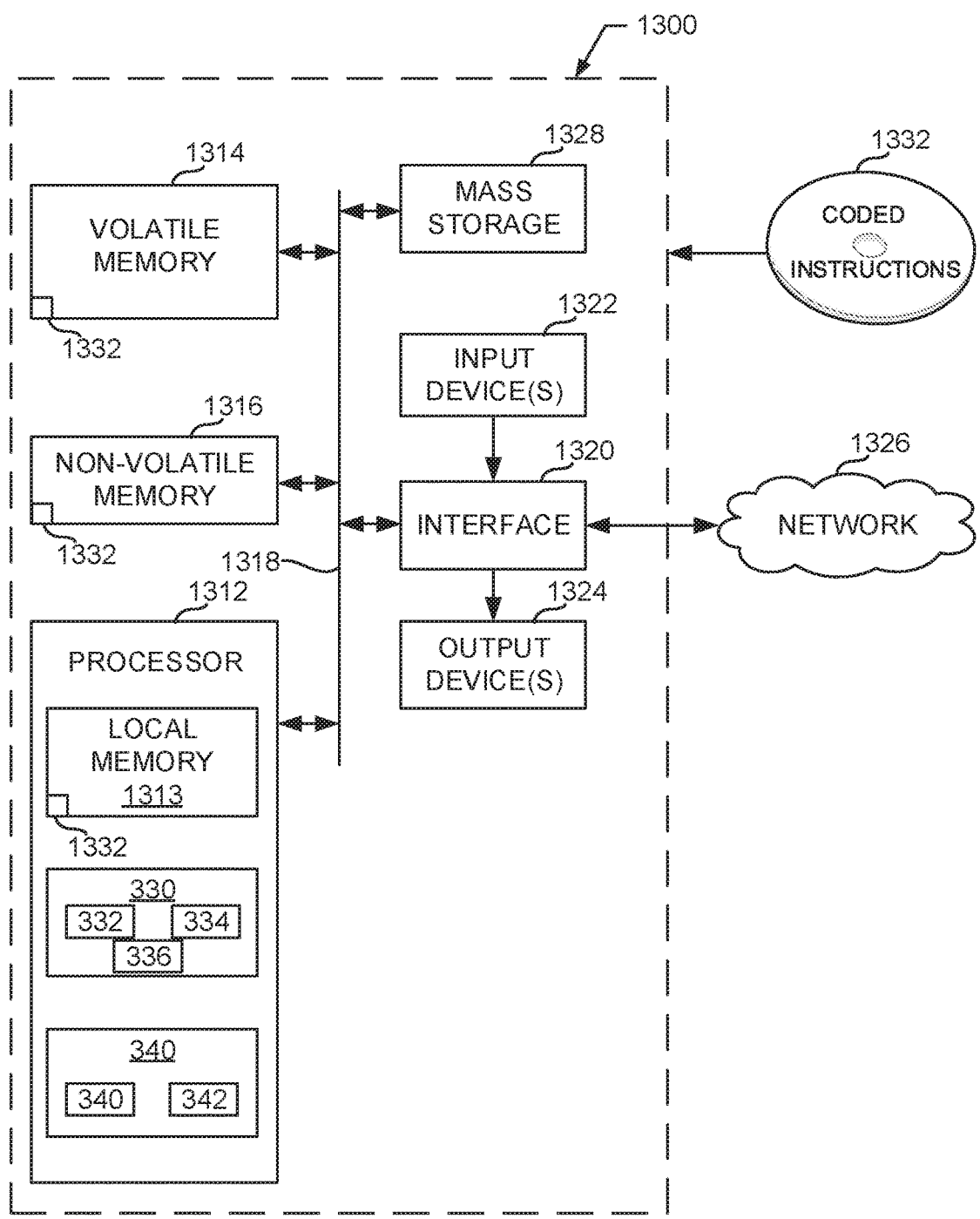
FIG. 13 is a block diagram of an example processor system that may be used to implement the systems, apparatus and methods described herein.

FIG. 13 is a block diagram of an example processor platform 1300 structured to execute the instructions of FIGS. 7 and 8 to implement the learning system 300 of FIG. 3. The processor platform 1300 can be, for example, a server, a personal computer, a workstation, a self-learning machine (e.g., a neural network), a mobile device (e.g., a cell phone, a smart phone, a tablet such as an iPad), a personal digital assistant (PDA), an Internet appliance, a DVD player, a CD player, a digital video recorder, a Blu-ray player, a gaming console, a personal video recorder, a set top box, a headset or other wearable device, or any other type of computing device.

The processor platform 1300 of the illustrated example includes a processor 1312. The processor 1312 of the illustrated example is hardware. For example, the processor 1312 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example machine learning engine 330, the example use analyzer 332, the example case learning analyzer 334, the machine learning model 336, the example user interface 340, the example user interface adjuster 340, the example user interface adjuster 342 and the example command recorder 344.

The processor 1312 of the illustrated example includes a local memory 1313 (e.g., a cache). The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1316 may be implemented by flash memory and/or any other desired type of memory device. Access to the main memory 1314, 1316 is controlled by a memory controller.

The processor platform 1300 of the illustrated example also includes an interface circuit 1320. The interface circuit 1320 may be implemented by any type of interface standard, such as an Ethernet interface, a universal serial bus (USB), a Bluetooth® interface, a near field communication (NFC) interface, and/or a PCI express interface.

In the illustrated example, one or more input devices 1322 are connected to the interface circuit 1320. The input device (s) 1322 permit(s) a user to enter data and/or commands into the processor 1312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1024 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1320 of the illustrated example, thus, typically includes a graphics driver card, a graphics driver chip and/or a graphics driver processor.

The interface circuit 1320 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1326. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, redundant array of independent disks (RAID) systems, and digital versatile disk (DVD) drives.

The machine executable instructions 1332 of FIGS. 7 and 8 may be stored in the mass storage device 1328, in the volatile memory 1314, in the non-volatile memory 1316, and/or on a removable non-transitory computer readable storage medium such as a CD or DVD.

From the foregoing, it will be appreciated that example methods, apparatus and articles of manufacture have been disclosed that enable adjustment of user interfaces based on machine learning techniques to save user time. In particular, examples disclosed herein can be implemented to save time for a reviewing physician that views medical images. Some examples disclosed herein enable more computationally efficient transfers of image data and/or files associated with user interfaces by utilizing models to predict user commands based on data context (e.g., learned contextual associations). As opposed to known user interface adjustments, which mainly develop an initial image hang or arrangement, examples disclosed herein learn and train models that encompass learning of a large extent of user/application behavior/interaction to examine an initial setup and subsequent interaction to provide a comprehensive model affecting operation of the whole application and not just the initial user interface setup. In other words, examples disclosed herein greatly improve the user interface by continuously adjusting the user interface setup based on contextual learning of medical data.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent. While examples disclosed herein are shown in relation to clinical imaging system, the examples can be implemented with any appropriate user interface application or user-interface driven data system.

What is claimed is:

1. An apparatus comprising:
   a use monitor including a processor to monitor, in a first session, user actions and medical content data pertaining to operation of a clinical image display to define training data; and
   a learning device including a processor to implement a learning network to develop a model for a subsequent session based on the training data in relationship to a context of the medical content data, the medical content data including medical case histories and diagnoses, the model developed by defining contextual patterns of the user actions in relationship to the medical case histories and the diagnoses, the learning device to adjust, prior to or during a second session subsequent the first session, at least one user interface element of a user interface based on the model, the at least one user interface element to be adjusted for use with subsequent medical case histories and diagnoses associated with the second session.

2. The apparatus as defined in claim 1, wherein the learning device is to define the context at least partially based on an image similarity analysis of images associated with the medical case histories and the diagnoses.

3. The apparatus as defined in claim 1, wherein the learning network is to analyze similarities of images of different medical cases in relationship to the medical case histories and the diagnoses.

4. The apparatus as defined in claim 1, wherein the content data includes metadata associated with a respective medical case.

5. The apparatus as defined in claim 1, wherein the adjustment of the at least one user interface element includes moving an icon or menu item displayed on the user interface.

6. The apparatus as defined in claim 1, wherein the adjustment of the at least one user interface element includes changing an order of icons or menu items displayed on the user interface.

7. The apparatus as defined in claim 1, wherein the adjustment of the at least one user interface element includes rearranging a sequence of medical images based on the medical case histories and the diagnoses.

8. The apparatus as defined in claim 1, wherein the adjustment of the at least one user interface element includes changing a sub-menu hierarchy of a sub-menu displayed on the user interface.

9. A method to adjust at least one user interface element of a user interface configuration pertaining to a clinical image display, the method comprising:
   monitoring, by executing instructions with a processor, user actions and medical content data during a first session of the clinical image display to define training data;
   developing, by executing instructions with the processor, a model for a subsequent session based on the user actions in relation to a context of the medical content data with a learning network, the model developed by defining contextual patterns of the user actions in relationship to medical histories and diagnoses of the medical content data; and
   adjusting, by executing instructions with the processor, the at least one user interface element of a user interface based on the model prior to or during a second session subsequent the first session, the at least one user interface element to be adjusted for use with subsequent medical case histories and diagnoses associated with the second session.

10. The method as defined in claim 9, further including performing, by executing instructions with the processor, a similarity analysis of medical images of different medical cases in relationship to medical case data to analyze the context of the medical content data.

11. The method as defined in claim 9, wherein the adjusting of the at least one user interface element includes moving an icon or menu item displayed on the user interface.

12. The method as defined in claim 9, wherein the adjusting of the at least one user interface element includes changing an order of icons or menu items displayed on the user interface.

13. The method as defined in claim 9, wherein the adjusting of the at least one user interface element includes rearranging a sequence of medical images based on the medical case histories and the diagnoses.

14. The method as defined in claim 9, wherein the adjusting of the at least one user interface element includes changing a sub-menu hierarchy of a sub-menu displayed on the user interface.

15. A tangible non-transitory machine readable medium comprising instructions, which when executed, cause a processor to at least:
   define training data based on monitored user actions in relationship to a context of medical content data during operation of a clinical image display in a first session;
   develop, by a training network, a model for a subsequent session based on the training data, the model developed by defining contextual patterns of the user actions in relation to a context of the medical content data with a learning network, the model developed by defining contextual patterns of the user actions in relationship to medical histories and diagnoses of the medical content data; and
   adjust at least one user interface element of a user interface of the clinical image display based on the model prior to or during a second session subsequent the first session, the at least one user interface element of the user interface to be adjusted for use with subsequent medical case histories and diagnoses associated with the second session.

16. The non-transitory machine readable medium as defined in claim 15, wherein the processor is further caused to perform a similarity analysis of medical images of different medical cases in relationship to medical case data to analyze the context of the medical content data.

17. The non-transitory machine readable medium as defined in claim 15, wherein the adjustment of the at least one user interface element includes moving an icon or menu item displayed on the user interface.

18. The non-transitory machine readable medium as defined in claim 15, wherein the adjustment of the at least one user interface element includes changing an order of icons or menu items displayed on the user interface.

19. The non-transitory machine readable medium as defined in claim 15, wherein the adjustment of the at least one user interface element includes rearranging a sequence of medical images based on the medical case histories and the diagnoses.

20. The non-transitory machine readable medium as defined in claim 15, wherein the adjustment of the at least one user interface element includes changing a sub-menu hierarchy of a sub-menu displayed on the user interface.

* * * * *

UNITED STATES PATENT AND TRADEMARK OFFICE
CERTIFICATE OF CORRECTION

| | |
|---|---|
| PATENT NO. | : 11,461,596 B2 |
| APPLICATION NO. | : 17/070468 |
| DATED | : October 4, 2022 |
| INVENTOR(S) | : Joy |

It is certified that error appears in the above-identified patent and that said Letters Patent is hereby corrected as shown below:

In the Claims

In Column 18, Claim 15, Line 1, delete "tangible".

Signed and Sealed this
Seventh Day of March, 2023

Katherine Kelly Vidal
*Director of the United States Patent and Trademark Office*